United States Patent
Raybuck

(10) Patent No.: US 7,651,481 B2
(45) Date of Patent: Jan. 26, 2010

(54) SELF-SEALING MALE CONNECTOR DEVICE WITH COLLAPSIBLE BODY

(75) Inventor: John Raybuck, Los Angeles, CA (US)

(73) Assignee: CareFusion 303 Inc., San Diego, CA (US)

( * ) Notice: Subject to any disclaimer, the term of this patent is extended or adjusted under 35 U.S.C. 154(b) by 700 days.

(21) Appl. No.: 11/026,002

(22) Filed: Dec. 30, 2004
(Under 37 CFR 1.47)

(65) Prior Publication Data

US 2006/0149213 A1    Jul. 6, 2006

(51) Int. Cl.
*A61M 5/00* (2006.01)
*A61M 31/00* (2006.01)
*A61M 5/14* (2006.01)

(52) U.S. Cl. ............... 604/246; 604/500; 604/905; 604/256; 604/213

(58) Field of Classification Search ............. 604/533, 604/30, 553, 256, 246, 213, 905, 236; 251/149.1, 251/150, 162, 203, 206, 149.6
See application file for complete search history.

(56) References Cited

U.S. PATENT DOCUMENTS

| | | |
|---|---|---|
| 2,931,668 A | 4/1960 | Baley |
| 2,968,497 A | 1/1961 | Treleman |
| 3,127,892 A | 4/1964 | Bellamy, Jr. et al. |
| 3,304,047 A | 2/1967 | Martin |
| 3,334,860 A | 8/1967 | Bolton, Jr. |
| 3,986,508 A | 10/1976 | Barrington |
| 4,066,067 A | 1/1978 | Micheli |
| 4,080,965 A | 3/1978 | Phillips |
| 4,121,585 A | 10/1978 | Becker, Jr. |
| 4,133,441 A | 1/1979 | Mittleman et al. |
| 4,195,632 A | 4/1980 | Parker et al. |
| 4,233,982 A | 11/1980 | Bauer et al. |
| 4,245,635 A | 1/1981 | Kontos |
| 4,326,569 A * | 4/1982 | Vaillancourt ............... 141/383 |
| 4,340,049 A | 7/1982 | Munsch |
| 4,379,458 A | 4/1983 | Bauer et al. |
| 4,387,879 A | 6/1983 | Tauschinski |
| 4,397,442 A | 8/1983 | Larkin |
| 4,457,749 A | 7/1984 | Bellotti et al. |

(Continued)

FOREIGN PATENT DOCUMENTS

WO    WO 97/00702    1/1997

OTHER PUBLICATIONS

International Search Report—International Application No. PCT/US2005/045924 International Filing Date: Dec. 16, 2005.

*Primary Examiner*—Kevin C Sirmons
*Assistant Examiner*—Michael J Anderson
(74) *Attorney, Agent, or Firm*—McDermott Will & Emery LLP

(57) ABSTRACT

A self-sealing male connector device for connection with a female Luer connector. The device has an elongated male body configured with lengthwise relatively rigid and flexible wall segments cooperating to allow the body to be radially compressed from an expanded configuration to a contracted configuration. A closure cap formed with a resealable aperture is disposed on the distal end of the male body so as to be responsive to the compression of the male body. The relatively flexible wall segments may be installed within notches in the male body or be formed integral with the relatively rigid wall segments.

20 Claims, 12 Drawing Sheets

U.S. PATENT DOCUMENTS

| | | | |
|---|---|---|---|
| 4,511,359 A | 4/1985 | Vaillancourt | |
| 4,623,332 A | 11/1986 | Lindmayer et al. | |
| 4,662,878 A | 5/1987 | Lindmayer | |
| 4,723,603 A | 2/1988 | Plummer | |
| 4,774,964 A | 10/1988 | Bonaldo | |
| 4,774,965 A | 10/1988 | Rodriguez et al. | |
| 4,781,702 A | 11/1988 | Herrli | |
| 4,816,024 A | 3/1989 | Sitar et al. | |
| 4,834,271 A | 5/1989 | Litwin | |
| 4,862,913 A | 9/1989 | Wildfang | |
| 4,883,483 A | 11/1989 | Lindmayer | |
| 4,915,687 A | 4/1990 | Sivert | |
| 4,917,669 A | 4/1990 | Bonaldo | |
| 4,935,010 A | 6/1990 | Cox et al. | |
| 4,950,260 A | 8/1990 | Bonaldo | |
| 5,006,114 A | 4/1991 | Rogers et al. | |
| 5,065,783 A | 11/1991 | Ogle, II | |
| 5,070,885 A | 12/1991 | Bonaldo | |
| 5,098,385 A | 3/1992 | Walsh | |
| 5,108,376 A | 4/1992 | Bonaldo | |
| 5,122,123 A | 6/1992 | Vaillancourt | |
| 5,139,483 A | 8/1992 | Ryan | |
| 5,147,333 A | 9/1992 | Raines | |
| 5,154,703 A | 10/1992 | Bonaldo | |
| RE34,223 E | 4/1993 | Bonaldo | |
| 5,199,948 A | 4/1993 | McPhee | |
| 5,201,725 A | 4/1993 | Kling | |
| 5,203,775 A | 4/1993 | Frank et al. | |
| 5,211,634 A | 5/1993 | Vaillancourt | |
| 5,215,537 A | 6/1993 | Lynn et al. | |
| 5,215,538 A | 6/1993 | Larkin | |
| 5,242,393 A | 9/1993 | Brimnall et al. | |
| 5,251,873 A | 10/1993 | Atkinson et al. | |
| 5,269,771 A | 12/1993 | Thomas et al. | |
| 5,273,533 A | 12/1993 | Bonaldo | |
| 5,279,571 A | 1/1994 | Larkin | |
| 5,281,206 A | 1/1994 | Lopez | |
| 5,284,475 A | 2/1994 | Mackal | |
| 5,295,657 A | 3/1994 | Atkinson | |
| 5,306,243 A | 4/1994 | Bonaldo | |
| 5,330,450 A | 7/1994 | Lopez | |
| 5,334,159 A | 8/1994 | Turkel | |
| 5,344,414 A | 9/1994 | Lopez et al. | |
| 5,360,413 A | 11/1994 | Leason et al. | |
| 5,370,636 A | 12/1994 | Von Witzleben | |
| 5,380,306 A | 1/1995 | Brinon | |
| 5,385,372 A | 1/1995 | Utterberg | |
| 5,390,898 A | 2/1995 | Smedley et al. | |
| 5,395,348 A | 3/1995 | Ryan | |
| 5,395,352 A * | 3/1995 | Penny | 604/256 |
| 5,397,314 A | 3/1995 | Farley et al. | |
| 5,400,500 A | 3/1995 | Behnke et al. | |
| 5,401,245 A | 3/1995 | Haining | |
| 5,402,982 A | 4/1995 | Atkinson et al. | |
| 5,405,323 A | 4/1995 | Rogers et al. | |
| 5,405,331 A | 4/1995 | Behnke et al. | |
| 5,405,333 A | 4/1995 | Richmond | |
| 5,411,499 A | 5/1995 | Dudar et al. | |
| 5,417,673 A | 5/1995 | Gordon | |
| 5,423,791 A | 6/1995 | Bartlett | |
| 5,425,465 A | 6/1995 | Healy | |
| 5,433,330 A | 7/1995 | Yatsko et al. | |
| 5,439,451 A | 8/1995 | Collinson et al. | |
| 5,441,487 A | 8/1995 | Vedder | |
| 5,456,668 A | 10/1995 | Ogle, II | |
| 5,456,675 A | 10/1995 | Wolbring et al. | |
| 5,464,399 A | 11/1995 | Boettger | |
| 5,470,319 A | 11/1995 | Mayer | |
| 5,470,327 A | 11/1995 | Helgren et al. | |
| 5,474,536 A | 12/1995 | Bonaldo | |
| 5,480,393 A | 1/1996 | Bommarito | |
| 5,492,147 A | 2/1996 | Challender et al. | |
| 5,501,426 A | 3/1996 | Atkinson et al. | |
| 5,514,117 A | 5/1996 | Lynn | |
| 5,518,026 A | 5/1996 | Benjey | |
| 5,520,665 A | 5/1996 | Fleetwood | |
| 5,533,708 A | 7/1996 | Atkinson et al. | |
| 5,533,983 A | 7/1996 | Haining | |
| 5,540,661 A | 7/1996 | Tomisaka et al. | |
| 5,549,566 A | 8/1996 | Elias et al. | |
| 5,549,577 A | 8/1996 | Siegel et al. | |
| 5,549,651 A | 8/1996 | Lynn | |
| 5,552,118 A | 9/1996 | Mayer | |
| 5,555,908 A | 9/1996 | Edwards et al. | |
| 5,569,235 A | 10/1996 | Ross et al. | |
| 5,573,516 A | 11/1996 | Tyner | |
| 5,575,769 A | 11/1996 | Vaillancourt | |
| 5,578,059 A | 11/1996 | Patzer | |
| 5,584,819 A | 12/1996 | Kopfer | |
| 5,597,536 A | 1/1997 | Mayer | |
| 5,616,129 A | 4/1997 | Mayer | |
| 5,616,130 A | 4/1997 | Mayer | |
| RE35,539 E | 6/1997 | Bonaldo | |
| 5,645,538 A | 7/1997 | Richmond | |
| 5,674,206 A | 10/1997 | Allton et al. | |
| 5,676,346 A | 10/1997 | Leinsing | |
| 5,685,866 A | 11/1997 | Lopez | |
| 5,738,144 A | 4/1998 | Rogers | |
| RE35,841 E | 7/1998 | Frank et al. | |
| 5,782,816 A | 7/1998 | Werschmidt et al. | |
| 5,806,831 A | 9/1998 | Paradis | |
| 5,820,601 A | 10/1998 | Mayer | |
| 5,839,715 A | 11/1998 | Leinsing | |
| 5,848,994 A | 12/1998 | Richmond | |
| 6,029,946 A | 2/2000 | Doyle | |
| 6,050,978 A | 4/2000 | Orr et al. | |
| 6,068,011 A | 5/2000 | Paradis | |
| 6,079,432 A | 6/2000 | Paradis | |
| 6,106,502 A | 8/2000 | Richmond | |
| 6,113,068 A | 9/2000 | Ryan | |
| 6,142,446 A | 11/2000 | Leinsing | |
| 6,206,860 B1 | 3/2001 | Richmond | |
| 6,290,206 B1 | 9/2001 | Doyle | |
| 6,299,132 B1 | 10/2001 | Weinheimer et al. | |
| 6,344,033 B1 * | 2/2002 | Jepson et al. | 604/256 |
| 6,485,472 B1 | 11/2002 | Richmond | |
| 6,541,802 B2 | 4/2003 | Doyle | |
| 6,745,998 B2 | 6/2004 | Doyle | |
| 7,037,303 B2 * | 5/2006 | Beaufore et al. | 604/537 |
| 7,040,598 B2 * | 5/2006 | Raybuck | 251/149.1 |
| 7,118,560 B2 * | 10/2006 | Bonaldo | 604/537 |
| 7,140,592 B2 * | 11/2006 | Phillips | 251/149.6 |
| 2002/0138047 A1 * | 9/2002 | Lopez | 604/249 |
| 2003/0032940 A1 | 2/2003 | Doyle | |
| 2003/0060779 A1 | 3/2003 | Richmond | |
| 2003/0060804 A1 | 3/2003 | Vaillancourt | |
| 2003/0136932 A1 | 7/2003 | Doyle | |
| 2003/0183795 A1 | 10/2003 | Doyle | |
| 2004/0006330 A1 * | 1/2004 | Fangrow, Jr. | 604/533 |
| 2004/0124389 A1 | 7/2004 | Phillips | |
| 2006/0149213 A1 * | 7/2006 | Raybuck | 604/500 |

* cited by examiner

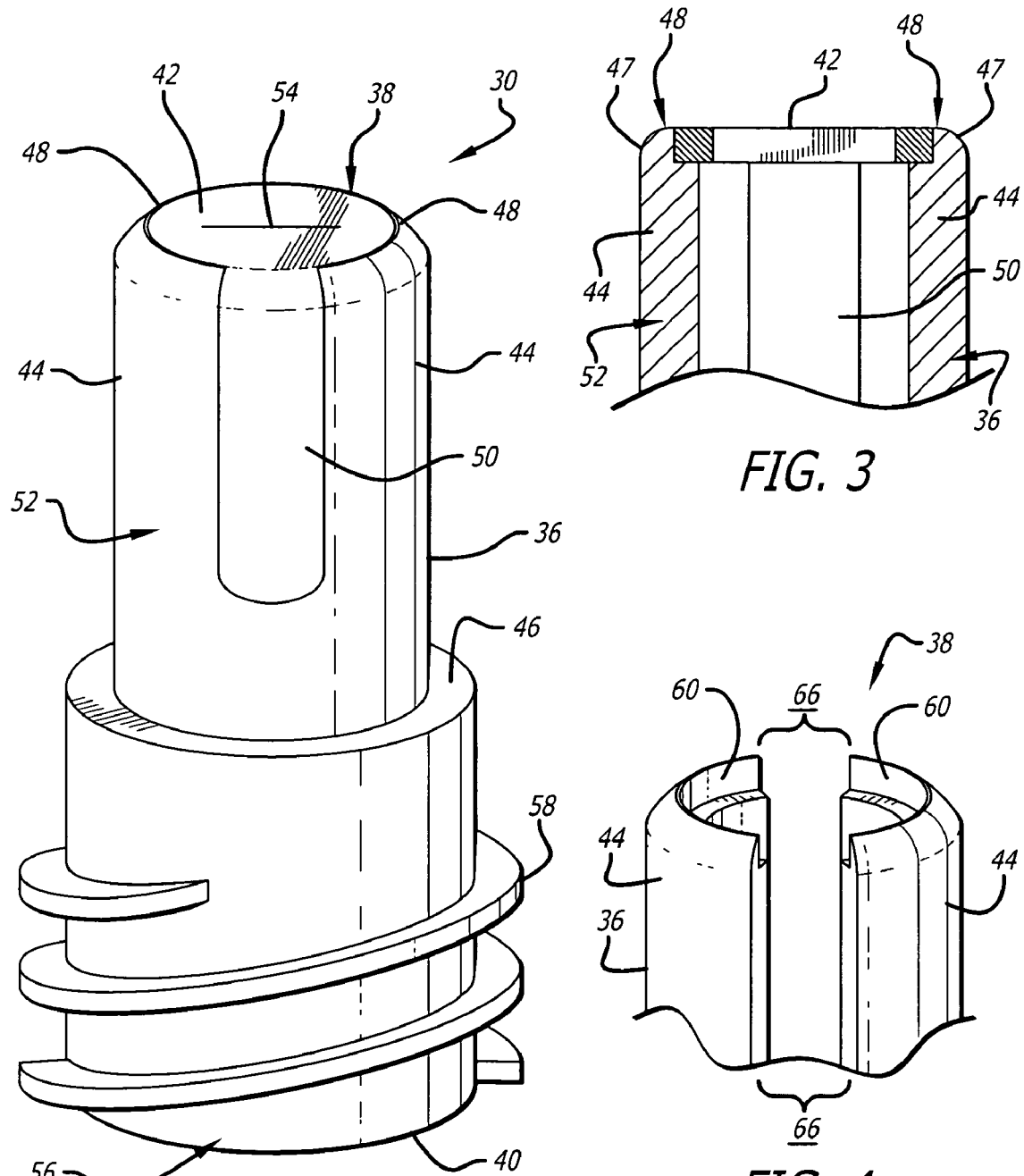

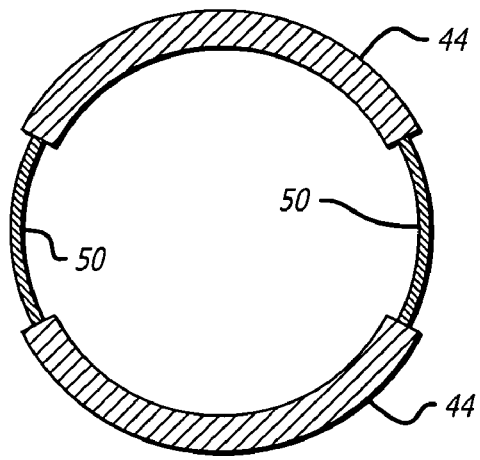
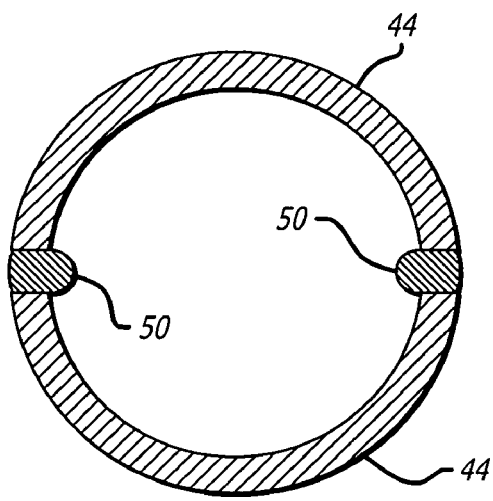
FIG. 13  FIG. 14
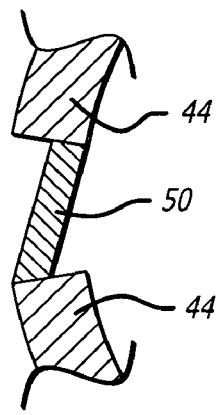
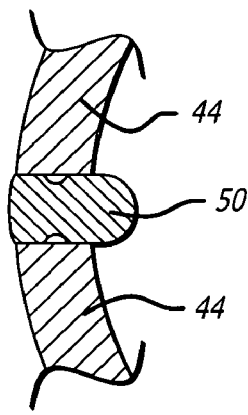
FIG. 15  FIG. 16
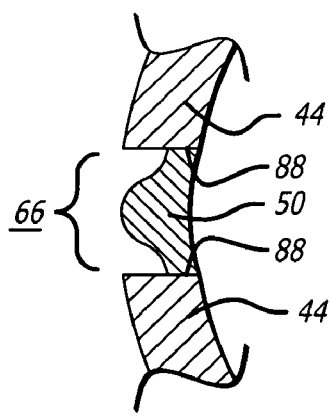
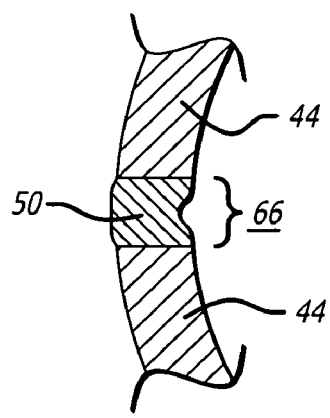
FIG. 17  FIG. 18

SELF-SEALING MALE CONNECTOR DEVICE WITH COLLAPSIBLE BODY

BACKGROUND OF THE INVENTION

The present invention generally relates to medical connectors used in conducting medical fluids and more specifically to self-sealing male connectors.

The self-sealing medical connectors presently known and used in the art are generally designed to be connected to a patient's intravenous ("IV") or gas sampling line, drug or solution source, or other medical device such that the connector's seal operates to trap all fluid on the side of the connector toward the patient or other device. As such, the typical connector has an unsealed male Luer connector on one end that remains connected to the patient's IV line, fluid source or other device and a self-sealing female connector on the opposite free end of the connector through which a syringe or other such device may be engaged. The self-sealing female connector typically has an internal valve that is opened upon connection with a male connector and which automatically closes upon disconnection from the male connector.

In use, the syringe or other device having a male connector is connected to the female end of the connector to push or pull fluids through the female connector, as when medications are dispensed within a patient's I.V. line. The syringe or other device is configured with a male connector so as to engage the self-sealing female connector and cause the male connector's central boss to contact the female connector's seal membrane, opening the internal valve of the female connector and creating a fluid path through the female connector. After the necessary fluids have been dispensed or withdrawn, the syringe is removed and the internal valve in the female needle-free connector closes to reseal the female connector and trap all bodily fluids, including any just-dispensed medications, on the patient side of the connector. However, the male connector of the syringe typically does not include an internal valve and any residual fluids remaining therein are unsealed and exposed.

In the medical industry, there are applications in which the fluid being dispensed from or drawn into the syringe or other device or container must itself be at all times sealed off and exposure of the care giver to such fluid prevented or at least minimized. For example, in the area of nuclear medicine where radioactive isotopes are administered to patients, it is critical that exposure to the isotopes be minimized for the safety of both the care giver and the patient. A further example includes collecting blood from a patient, where it is important to prevent exposure of the blood remaining in the collection device to the care giver.

Yet a further example is in the oncology area where certain drugs have great beneficial effect when confined to the circulatory system of a patient, yet are harmful to the skin or other tissues of a patient. Such drugs must be carefully controlled so that they do not reach tissues that may be harmed. Transferring such drugs from one container to another or to the patient's fluid line can be hazardous if seals are not present.

For these purposes, a different self-sealing, needle-free male Luer connector design is desirable. Where even the slightest amount of contact between such strong medical fluids and the clinician or the patient's outer tissue is to be avoided, it would be highly beneficial to provide a male connector that is able to minimize the existence of such fluids on its outer surfaces. In the case where such fluids inadvertently reside on such outer surfaces, such a connector should provide a means of removing the fluids form those surfaces.

It is becoming more and more common for connectors to use Luer shapes. This is because an international standard has been adopted for such shapes; see ISO No. 594. Such Luer shapes have a tapered outer surface for male connectors and a complementary tapered inner surface for female connectors. Such tapering permits connectors having less precise dimensions to still successfully mate for fluid transfer. For more secure connection, threads or thread elements have been added to the outer surface surrounding the female connector's opening and a threaded collar has been added about the male Luer connector. The threaded collar may freely rotate or may be fixed in position about the male Luer connector. Because of the wide availability of female connectors and female valve ports, it would be desirable to provide a self-sealing male connector having a Luer shape.

Hence, those skilled in the art have recognized a need for a self-sealing male connector to seal off residual fluids therein before and after connection to a female connector. Such a self-sealing male connector may be connected to or formed as part of a syringe or other device, or formed on a blood collection device, or may be used with tubing or other devices for controllably conducting medical fluids, including more dangerous fluids that are toxic or corrosive. The present invention fulfills these needs and others.

SUMMARY OF THE INVENTION

The present invention is directed to a self-sealing male connector device for needle-free connection to a female connector device. The male connector device includes a male body formed by a male tubular wall having a first end and a second end with an internal fluid passage that puts the first and second ends in fluid communication with one another. The fully constructed tubular wall is continuous from the first end to the second end, meaning that there are no gaps in the tubular wall itself. The first or distal end of the tubular wall includes a rim that defines an opening, wherein the rim flexes between a natural, at-rest, expanded configuration when it is not engaged with a female connector device and a contracted configuration when it is engaged with a female connector device. A cap is disposed at the rim and formed with a resealable aperture, such as a slit, that is closed when the rim is in the natural, expanded configuration and opened when the rim is in the contracted configuration. The rim flexes from the natural configuration to the contracted configuration when the male body is inserted into the female connector device.

In another aspect, the continuous tubular wall of the male body is formed with at least a first axial segment and a second axial segment, wherein the second axial segment has a greater flexibility than the first axial segment. The second axial segment may have a lesser wall thickness than the first axial segment, giving the second axial segment a greater flexibility than the first axial segment and permitting the male body to contract when engaged with a female connector device. In another aspect, the second axial segment may be formed of a resilient material constituting a web that has a greater flexibility than the first axial segment.

In another aspect, the continuous tubular wall is mounted to a base comprising the second or proximal end and at least two spaced-apart, relatively rigid wall segments are mounted to the base and project axially in the first or distal direction in a cantilever-type manner. The male body comprises notches of gaps formed between the rigid wall segments that are filled with flexible wall segments to connect the rigid wall segments together and to form a continuous tubular body to conduct fluids. The flexible wall segments allow the rigid wall segments to flex radially inward into the contracted configuration when engaging with a female connector device.

In yet another aspect, a connector is formed at the second or proximal end of the male connector device. The connector may be configured as a female Luer connector, a blood collection device, or other connector used in the medical industry. This connector can be used to attach a syringe or other such medical device to the male connector device.

In use, the male connector device may have a male Luer body to be inserted into to a female Luer connector. When not engaged with a female connector, the male connector device is in its natural configuration with, in one aspect, its exterior diameter that is larger than the interior diameter of the female connector. In the natural configuration, the resealable aperture of the closure cap of the male connector device is closed to prevent the flow of fluids therethrough. Once the male connector device is inserted into the female connector, the smaller interior diameter of the female connector causes the rim portion of the male connector device to contract or flex inward, thereby opening the resealable aperture of the cap to allow fluid to flow therethrough. The male connector device is then removed or pulled from the female connector, allowing the rim portion to expand outward toward the natural configuration and causing the resealable aperture of the closure cap to close. With this design, the male connector device seals off residual fluids therein before and after connection to the female Luer connector.

These and other features and advantages of the present invention will become apparent from the following detailed description of the preferred embodiments which, taken in conjunction with the accompanying drawings, illustrate by way of example the principles of the invention.

BRIEF DESCRIPTION OF THE DRAWINGS

FIG. 2 is an enlarged perspective view of an exemplary embodiment of the self-sealing male connector device of the present invention, the male connector device including an elongated male body and a flexible closure cap;

FIG. 3 is a cross-section view of the distal, or first, end of the male body of the connector device shown in FIG. 2 in which the chamfered outer edge is visible and showing a mounting ridge for the closure cap;

FIG. 4 is an enlarged perspective view of the mounting ridge formed at the distal end of the male body shown in FIG. 2 with the closure cap removed;

FIGS. 13 through 18 present radial cross-sectional views of different webbing configurations disposed between the relatively rigid walls of the male body member;

DETAILED DESCRIPTION OF THE PREFERRED EMBODIMENTS

Figure 1:
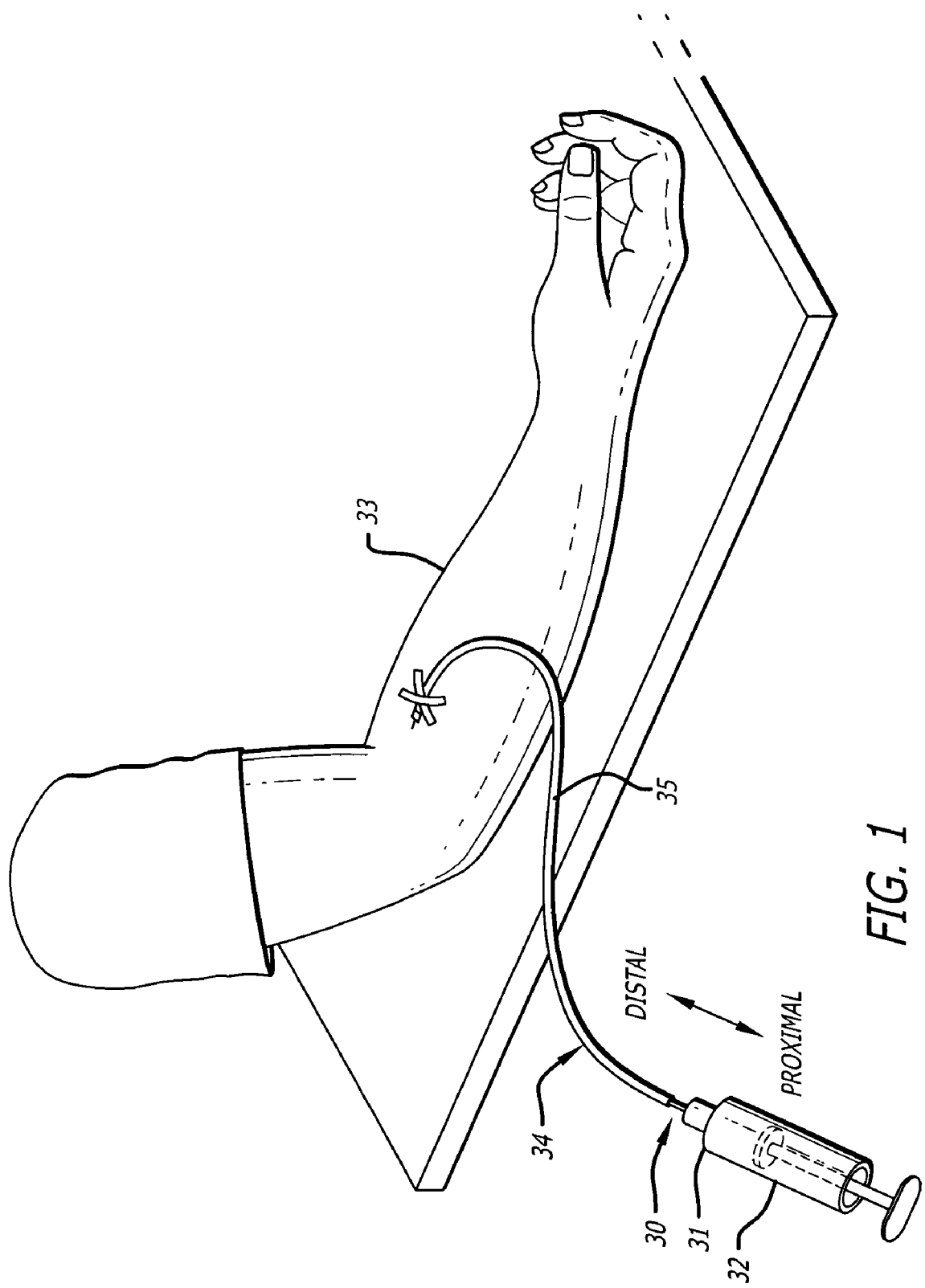
FIG. 1 is a simplified pictorial illustration of a patient IV interface operative in connection with an exemplary embodiment of the self-sealing male Luer connector device of the present invention.

Referring now in more detail to the drawings for purposes of illustration, wherein like reference numerals designate corresponding or like elements among the several views, there is shown in the illustration of FIG. 1, a self-sealing male Luer connector device 30 in accordance with aspects of the present invention mounted on the distal end 31 of a syringe 32 and operatively connected to the proximal end of a patient IV fluid administration set 34 for the administration or withdrawal of fluids through an IV line. It should be noted that throughout this specification, "distal" refers to the direction toward the patient 33 and "proximal" refers to the direction away from the patient, or toward the collection or dispensing device. These relative directions are indicated in FIG. 1 and other figures and are provided only for the purpose of reference and of further clarity in illustration of embodiments of the invention and not for the purpose of limitation.

Referring to FIG. 2, a perspective view is shown of an embodiment of the self-sealing male Luer connector device 30 of FIG. 1. In this embodiment, the male connector device has an elongated male body portion 36 with a first or distal end 38 and a second or proximal end 40. The male connector device also includes a flexible closure cap 42 that is disposed at the first end. The male body portion is formed with a plurality of relatively rigid wall segments 44 extending axially from a base 46 and terminating distally at the first end in rim elements 48 that cooperate to support the closure cap. The rim elements have radiused or chamfered exterior distal edges 47 as shown more clearly in FIG. 3 to facilitate the insertion of the male connector device into a female Luer connector. Returning to FIG. 2, disposed between the relatively rigid wall segments and joining them are relatively flexible wall segments 50 that complete the tubular body and form an hermetic seal. Together, the wall segments 44 and 50 form a continuous tubular wall 52 from the distal end to the proximal end of the male body portion. In a preferred embodiment, the closure cap and the flexible wall segments are manufactured as one continuous piece by co-injection molding, but it is possible to manufacture the cap and the wall segments separately and bond them together.

Disposed at the proximal or second end 40 of the male connector device 30 is a conventional female Luer connector 56, though it will be appreciated that a variety of other connectors and devices, such as simply a tubing connection or a syringe, may be employed instead. The base 46 is located between the distally-extending male body portion and the proximally-extending female Luer connector. The base provides a transition between the larger outer diameter of the female connector and the smaller diameter of the male body portion. In other embodiments where the proximal end of the male connector device is smaller in diameter that that shown for the female connector in FIG. 2, the base may be the same diameter as the male body portion or may have an even different configuration. The female Luer connector end includes standard external threads 58, although in some applications, threads may not be necessary.

Referring still to FIG. 2, the closure cap 42 of the self-sealing male connector device 30 has a generally circular perimeter in this embodiment, corresponding to an opening formed at the distal end 38 of the male body portion 36. The closure cap is formed of a membrane that includes a resealable aperture 54 that is closed to form a seal against fluid flow when the body is in its natural or "at-rest" configuration as shown. In a preferred embodiment, the resealable aperture is a slit as shown in the figures. As is well known, a slit does not permit the passage of fluid in its natural or "at rest" configuration. In order to open the slit and permit fluid flow through the male connector device upon engaging it with a female connector, the slit is oriented in regard to the relatively rigid wall segments 44 such that one end of the slit is adjacent one relatively rigid wall segment and the other end of the slit is adjacent an opposing relatively rigid wall segment. Thus when the relatively wall segments engage a smaller inner-diameter female connector and are forced to move toward each other, the ends of the slit will also be forced to move toward each other thus causing the slit to open.

Figure 5:
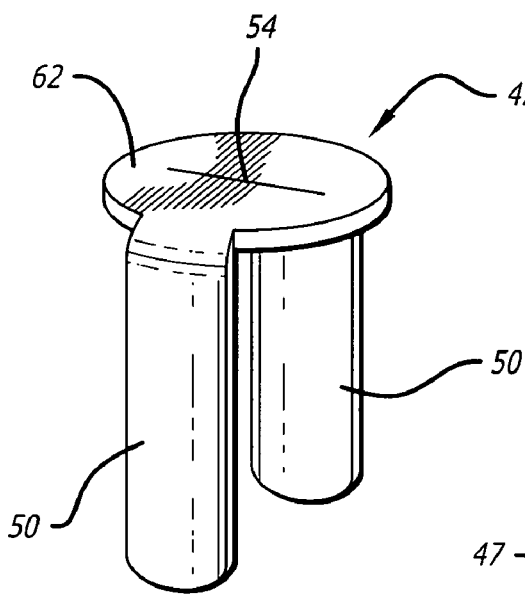
FIG. 5 is a perspective view of a closure cap that includes the flexible wall segments all formed as one piece.

In one embodiment, the closure cap 42 is dimensioned to fit along a ridge 60, best seen in FIG. 4, formed in the rigid wall segments 44 at the distal end 38. FIG. 4 shows the ridge without the presence of the closure cap while FIG. 3 shows a cross section view of the closure cap mounted in the male body portion 36. FIG. 5 presents a view of a flexible closure cap 42 that can be assembled at the distal end 38 of the rigid walls 44 of the male body portion 36 shown in FIG. 4 to form the assembled male Luer connector device 30 shown in FIG. 2. The closure cap includes the top surface 62 having the slit 54 as well as the flexible wall segments 50 shown in FIG. 2. In one embodiment, the diameter of the top surface is selected to be the same as the opening in the ridge 60 shown in FIG. 4. Because the resealable aperture 54 in the closure cap is a slit in this case, it remains closed to the flow of fluid when the closure cap is mounted to the male body portion. As discussed, an external force is required to open the slit and permit fluid flow. In another embodiment, the closure cap may be somewhat undersized in relation to the distal end 38 with a small amount of stretching required to mount the cap in the ridge. The cap will therefore be under some degree of tension thereby holding the slit closed more strongly. Thus when in the configuration of FIG. 2, the slit will resist the flow of fluid through it even more strongly.

Figure 6:
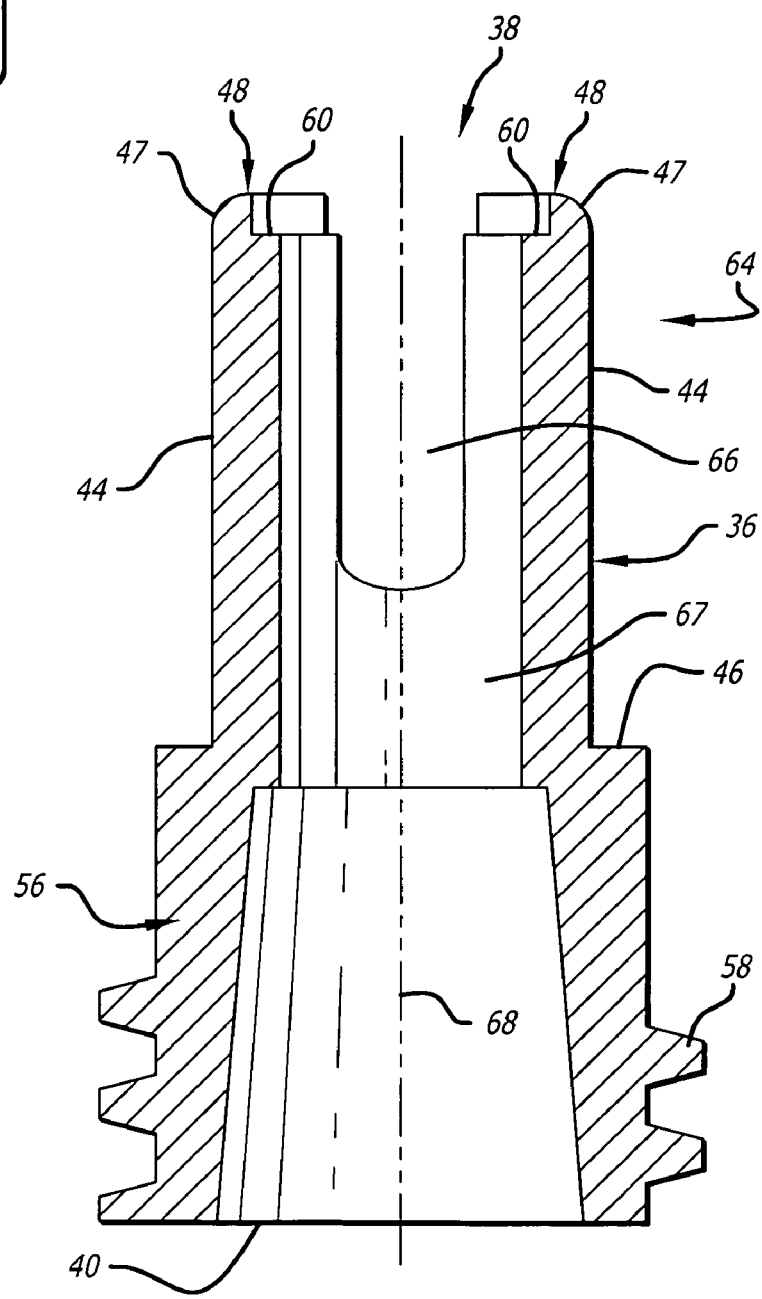
FIG. 6 is a side cross-section view of the housing of the male connector device of FIG. 2.

Turning now to the cross-sectional view in FIG. 6, the male body portion 36, the base 46, and the proximal end 40 may be considered to form the connector device housing 64. The housing defines a fluid flow passage 67 from its distal end 38 to its proximal end 40. The relatively rigid wall segments 44 are mounted to the base 46 in a cantilever manner as shown. To achieve this cantilever type manner of mounting, the relatively rigid wall segments have notches 66 formed in them from their distal ends and extending in the proximal direction to a selected length. In this embodiment, the locations of the notches are selected so that two relatively rigid wall segments are opposite each other. Because of these notches, the distal ends 38 of the opposing relatively rigid wall segments may be moved toward one another when subjected to external pressure directed inward toward the longitudinal axis 68 of the housing. However, when not subjected to inward pressure, the opposing relatively rigid wall segments tend to return to their natural at-rest configuration shown in FIG. 6. This tendency to return to their natural configuration will also return a closure cap 42 mounted at the distal end 38 to its natural at-rest configuration thereby closing the slit 54 in the cap, as shown in FIG. 2. However, to retain medical fluid within the male connector device 30, flexible wall segments 50 have been included within the notches 66, in this embodiment. In the one embodiment shown in FIG. 5, those flexible wall segments are provided by portions of the closure cap.

Figure 7:
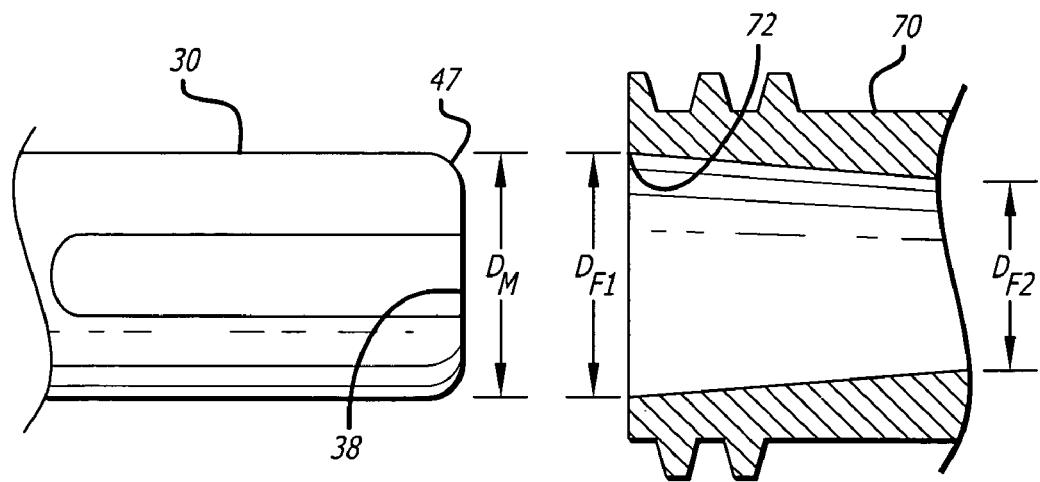
FIG. 7 is a side view in partial cross section of a male connector device in accordance with aspects of the invention aligned for connection with a female Luer connector showing the female connector device in cross section.
Figure 8:
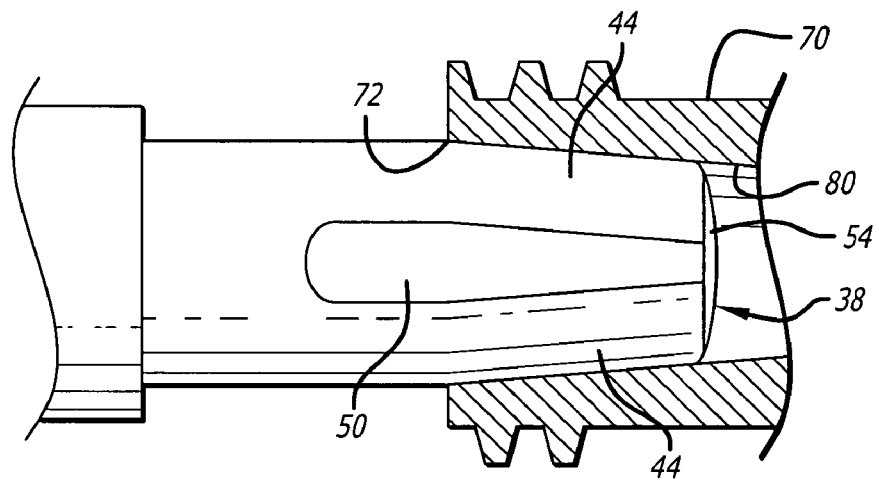
FIG. 8 is a side view in partial cross section of the male connector and female connector devices of FIG. 7 in which they are fully connected. The view also shows that the female connector device includes an inner engagement surface that is smaller in diameter than the male connector device to thereby contract the distal end of the male connector device and thereby activate the male connector device for fluid flow.
Figure 9:
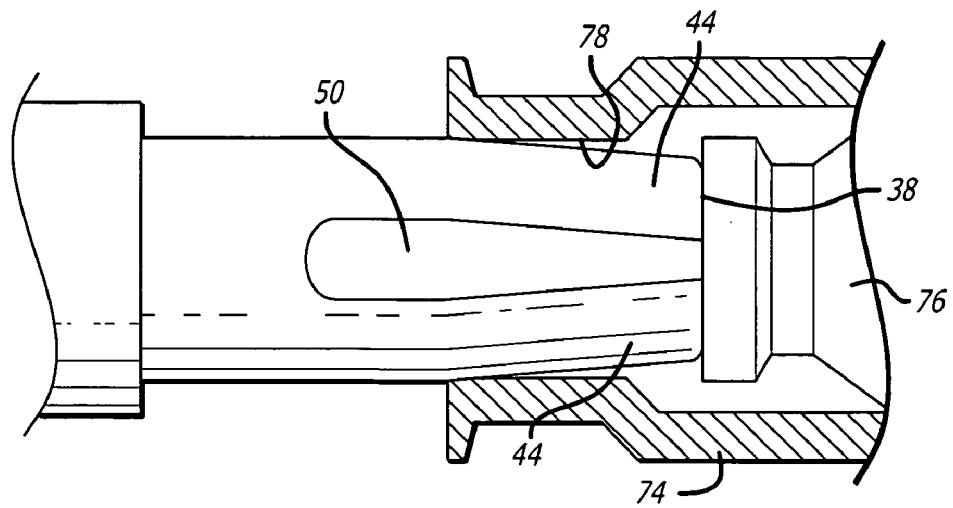
FIG. 9 is a side view in partial cross section of the male connector device of FIGS. 7 and 8 fully engaged with a female connector device having an internal valve mechanism in which the distal end of the male connector device has been contracted to thereby activate the male connector device for fluid flow.

Referring now to FIGS. 7 through 9, engagement of the male Luer connector device 30 with two different types of female Luer connector devices is shown. In FIG. 7, the male Luer connector device in accordance with aspects of the invention is aligned with the opening of a first type of female Luer connector device 70. In this embodiment of the female Luer connector device, there is no internal valve and the Luer opening 72 and channel is of the standard Luer taper and diameter. In particular, the female Luer opening has a diameter $D_{F1}$ that tapers down to a smaller diameter of $D_{F2}$ in the distal direction. This opening diameter $D_{F1}$ is equal to or larger than the diameter $D_M$ of the male connector device. In another embodiment, the diameter $D_M$ of the male connector device is larger than the opening diameter $D_{F1}$ of the female connector device. The chamfered, or otherwise rounded, edges 47 of the male connector device will assist in engaging the distal end 38 of the male connector device with the opening of the female connector device. The particular female Luer connector device shown in FIGS. 7 and 8 does not include a valve at or near its opening. However, the female Luer connector device 74 of FIG. 9 does include a valve, a portion of which is shown.

In FIG. 8, the male Luer connector device 30 has been fully engaged with the female connector device 70 so that the slit 54 of the male connector device has opened to permit fluid flow between the female and male connector devices. The distal end 38 of the male connector device has contracted as a result of its movement into the smaller diameter of the female Luer channel 72. The relatively rigid wall segments 44 of the male connector device have been bent inwardly to the contracted configuration at which the slit 54 opens to permit the flow of fluid through the male connector device.

Turning to FIG. 9, the male Luer connector device 30 in accordance with aspects of the invention has been fully engaged with a different type of female connector device 74. The female connector device of this figure includes an internal valve mechanism 76 that automatically opens to permit flow through the female connector device when the valve mechanism has been displaced into the housing of the female connector device as is shown in FIG. 9. The opening 78 of the second female connector device has a standard diameter so as to accept all standard Luer male connector devices; however, the standard Luer taper may or may not exist. In the configuration shown in FIG. 9, the standard female Luer taper does not exist at the opening 78 of the female connector device. However, in accordance with an aspect of the invention, the male body portion includes the relatively rigid wall segments 50. Because they are relatively rigid and are in a cantilever configuration, when they engage the opening of the female connecter device, which is of smaller diameter than the male connector device diameter, they will be forced to move inwardly toward each other into a contracted configuration as shown in FIG. 9, even though the female Luer taper is limited in length.

Upon disconnection of the male connector device 30 from either of the female connector devices 70 and 74 of FIGS. 7 through 9, the biasing effect of the elongated relatively rigid wall segments 44 of the male body portion 36 forces the rim elements 48 radially outwardly again toward the natural or "at-rest" configuration as shown in FIG. 2 causing the slit 54 to return to its natural closed configuration thereby resealing the aperture of the closure cap and preventing the flow of fluid through the male connector device. It will be appreciated that in this way, the self-sealing male connector device of the present invention closes and prevents flow therethrough both before and after connection with a female connector, or the like, while it opens and allows flow during connection. It will also be appreciated that the embodiment shown in FIG. 2 includes only two parts, the housing 64 and the closure cap 42. However, in another embodiment, the male connector device 30 may be made as one part through an injection molding process or other means.

Referring again to FIG. 8, the male connector 30 has been inserted into the female connector 70 to achieve an operational configuration and the distal end 38 of the male luer has contracted in diameter. The smaller inner diameter of the tapered female connector wall forces the rim elements 48 and rigid wall segments 44 to flex radially inwardly into the contracted configuration. In this embodiment, the diameter of the male body portion 36 and the length of the notches 66 are configured so that when the male connector is inserted within the female connector device to the point where the relatively rigid wall segments can flex no farther, the rigid and flexible wall segments 44 and 50 lay substantially flush against the inner female engagement surface 80 of the female connector device to achieve a generally surface-to-surface seal between the two connector devices.

Figure 10:
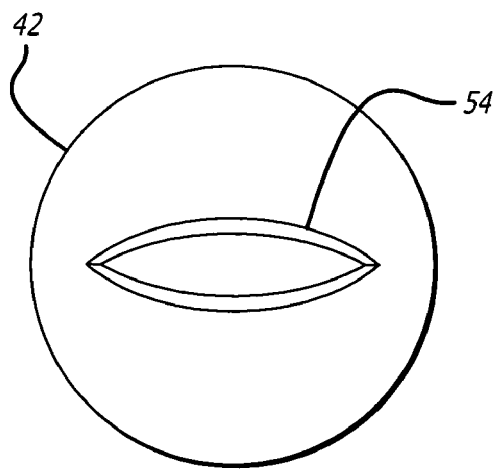
FIG. 10 is an end-on view of the distal end of the male connector device when in the contracted configuration presenting one embodiment of a flow path created through the closure cap.
Figure 11:
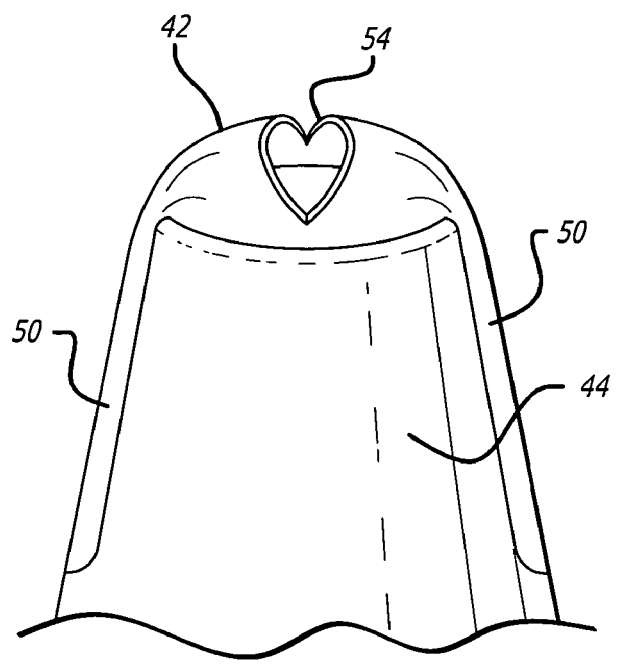
FIG. 11 is a perspective view of the distal end of a male connector device in accordance with aspects of the invention when the distal end is contracted due to connection with a smaller diameter female connector device and showing that as the diameter of the first end contracts, the diameter of the closure cap contracts and a center section of the closure cap containing the aperture is displaced in a longitudinal axial direction, in this case, it puckers axially outwards, thereby causing the aperture to open to permit fluid flow through the closure cap.
Figure 12:
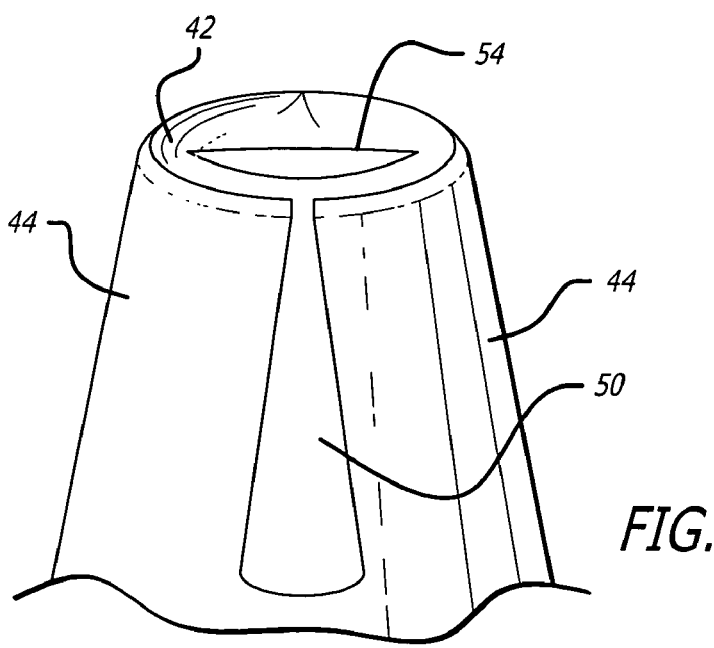
FIG. 12 is a perspective view of the distal end of a male connector device in accordance with aspects of the invention when the distal end is contracted due to connection with a smaller diameter female connector device and showing that as the diameter of the first end contracts, the diameter of the closure cap contracts and a center section of the closure cap containing the aperture is displaced in a longitudinal axial direction, in this case, it puckers axially inwards, thereby causing the aperture to open to permit fluid flow through the closure cap.

With reference now to FIGS. 10, 11, and 12, the effect on the slit 54 of collapsing the distal end 38 of the male connector device 30 is illustrated. FIG. 10 shows the overall shape of the opening created by compressing the slit such as by inserting the male connector device into the female connector 70 of FIG. 8. However, the entire distal end of the male connector device is contracted resulting in the closure cap 42 either flexing axially outward as shown in FIG. 11 or flexing axially inward, as shown in FIG. 12. In the case shown in FIG. 8 where the distal end of the male connector device does not abut any other device, the slit is more likely to assume the configuration shown in FIG. 11, i.e., an axially outward pucker. In the case shown in FIG. 9 where the distal end of the male connector device abuts another device, in this case the female valve mechanism, the slit is more likely to assume the configuration shown in FIG. 12, i.e., an axially inward pucker.

As used herein, "web" or "webbing" is meant to mean the flexible material located between the relatively rigid wall segments 44 that interconnects the rigid segments, whether that interconnecting material is formed from the same material as the rigid walls or is added and attached in some way.

It will be appreciated by those skilled in the art that the configuration of the male body portion 36 shown in FIGS. 2, 3, 4, and 6 is well-suited for the injection molding or co-injection molding manufacturing process. With such process, the body may be made in a relatively simple two-half mold cavity with a single linear core pull. The male body portion including the base 46 and the rigid wall segments 44 may be formed from a variety of plastic materials such as polyethylene, polypropylene, polycarbonate, UHMW, PVC, ABS, acrylic, nylon, POM, and K-resin. It follows that a wide range of radial biasing forces exerted by the free ends of the relatively rigid wall segments can be achieved by simply changing the material selection and/or adjusting the wall thickness of the body. As such, it will be appreciated that a variety of notch 66 sizes and configurations may also be employed without departing from the scope of the present invention. Moreover, the connector to be formed on the proximal end 40 of the male body portion, such as a conventional female Luer connector 56, may also be formed in the same molding operation to yield a single, integral housing 64.

The flexible wall segments 50 and the closure cap 42 may be formed of a single unitary construction in a molding or extrusion and die-cutting process and then installed on the male body portion 36 using a solvent bonding, ultrasonic welding, or other such assembly technique now known or later developed. Alternatively, the flexible wall segments 50 and closure cap 42 may be formed directly on the male body portion in an over-molding process as is known in the art, or they may be formed separately. The flexible wall segments 50 span and sealingly engage the respective notches 66 and the closure cap engages the ridge 60 shown in FIG. 4 so that it is flush with the rim elements 48 at the distal end 38 of the male body portion so as to make the tubular male body portion continuous and leak-proof about its complete circumference. The flexible wall segments are configured as thin-walled webs and along with the closure cap may be formed of several resilient materials such as thermoplastic elastomers, TPV, thermoplastic vulcanates, and thermoplastic silicone.

Turning now to FIGS. 13 through 23, various configurations of webbing located in the slots 66 in the male body portion 36 are shown. It should be appreciated that in another embodiment or embodiments, the slots 66 may extend for the length of the rigid wall segments 44. That is, they may extend from the base 46 to the distal end 38. In FIG. 13, there is shown a cross-sectional view of the male body portion at the distal end showing the relatively rigid wall segments and flexible wall segments in their natural configuration. That is, the male Luer connector device, of which they form a part, is not engaged with a female connector in this figure. FIG. 14 however presents a cross-sectional view of the same male body portion in which the same relatively rigid wall segments and flexible wall segments of FIG. 13 are in fact contracted due to being engaged with a female Luer connector. The relatively rigid wall segments 44 have been flexed radially inwardly towards each other in the general direction of arrows 68 and the flexible wall segments 50 have been compressed circumferentially and generally expanding radially outwardly into contact with the female Luer connector device's inner wall (see FIG. 8) and radially inwardly.

In FIGS. 13 and 14, the flexible wall segments 50 are attached to the centers of the rigid wall segments 44. In FIG. 15, the flexible wall segments are attached to alternate outer edges and inner edges of the rigid wall segments. In FIG. 15, the male Luer connector device is in its natural configuration not engaged (disengaged) with a female connector such as is shown in FIG. 7. In FIG. 16, the same male body portion is contracted due to being engaged with a female Luer connector, such as in FIG. 8. As in FIG. 14, the flexible wall segments form an outer surface coextensive with the outer surface of the rigid wall segments so that the interface between the female and male connector devices will not leak.

Although shown in the previous embodiments as having a constant thickness, the flexible wall segments may actually have a variable thickness. In FIG. 17, such an arrangement is shown. The flexible wall segment 50 in this embodiment has a non-uniform thickness that includes a thicker, centrally-located, radially outward oriented protrusion or ridge 86. The flexible wall segment 50 is installed so as to span the notch 66 substantially at the inside portion 88 of its edges. In this way, as the male connector device 30 is compressed so as to close the notch, the flexible wall segment 50b expands along its length radially outwardly so that the bend 80 is shifted radially outwardly and into contact with the inside surface of the female connector. By being pre-biased to fold or bend in a specific direction, here radially outwardly, it will be appreciated that the risk of the flexible wall segment 50b buckling or flexing in an unwanted direction is minimized.

The above are examples of cross-section configurations in the radial orientation that the flexible wall segments 50 may take. Other configurations are possible, the above are only examples.

Figure 19:
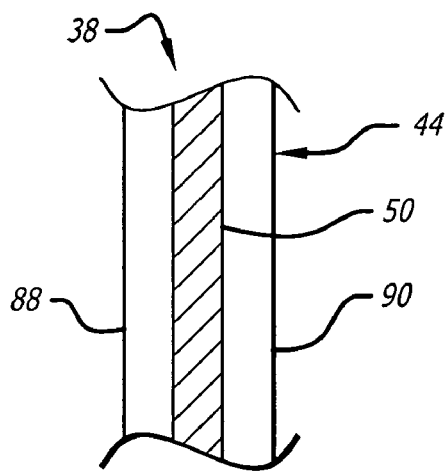
FIGS. 19 through 23 present axial cross-sectional views of different webbing configurations disposed between the relatively rigid walls of the male body member.

Configurations of the flexible wall segments 50 in the axial direction will now be discussed and shown. Referring now to FIG. 19, the flexible wall segment 50 is shown having a substantially uniform thickness along its length and is generally centered radially between the outside edge 90 and the inside edge 88 of the rigid wall segment 44.

Figure 20:
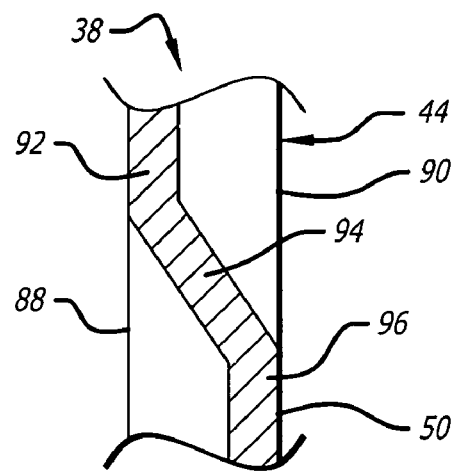

Turning to FIG. 20, the axial configuration of another embodiment of a flexible wall segment 50 is shown as having a distal upper portion 92 aligned with the inside edge 88 of the rigid wall segment 44, a intermediate proximally-angled portion 94, and a proximal lower portion 96 aligned with the outside edge 90 of the rigid wall segment. All of the flexible wall portions 92, 94, and 96 have a substantially uniform thickness. The flexible wall segment is configured to have a radially inset upper portion corresponding to the distal end of the male body portion and adjacent the rim elements that serves to facilitate inward movement of the rim elements to the contracted configuration and ease insertion of the male connector into the female connector. The proximally-angled portion of the flexible wall segment then smoothly transitions the wall to the outside edge of the male body portion so as to provide more resiliency within the lower, proximal section of the notch and to cause the compression and resulting radial expansion of the flexible wall segment to contribute to sealing the male connector within the female connector.

Figure 21:
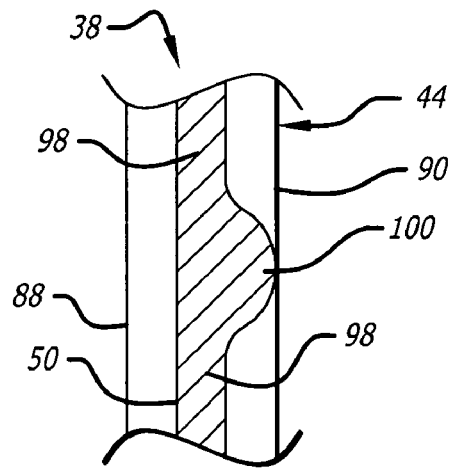

In FIG. 21, another embodiment of flexible wall segment 50 is shown in cross-section as having a substantially uniform lengthwise portion 98 generally centered between the outside edge 90 and the inside edge 88 with the exception of a radially outwardly projecting circumferential bulge 100 spaced proximally from the distal end 38. In the natural configuration of the male body portion 36 shown in FIG. 2, the outer extremity of the bulge is substantially aligned with the outside edge 90. It will be appreciated that as the male connector device 30 is inserted within the female connector and the rim elements are shifted toward the contracted configuration, the flexible web segments 50 will be compressed, thereby causing the bulge to expand radially outwardly and create an annular seal against the inside surface of the female connector.

Figure 22:
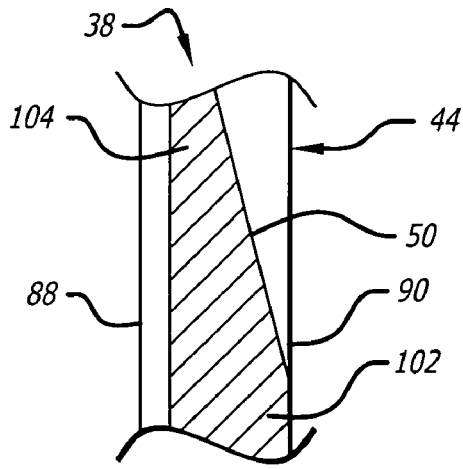

Turning now to FIG. 22, there is shown yet another embodiment of flexible wall segment 50 having a proximal lower portion 102 with a cross-sectional thickness that is slightly smaller than the wall thickness of the rigid wall segments 44. A distal upper portion 104 of the flexible wall segment is formed having a tapered outer surface so that the flexible wall segment becomes thinner toward the distal end 38. In this way, the radially inset distal portion of the flexible wall segment facilitates compression of the distal end of the male body portion 36.

Figure 23:
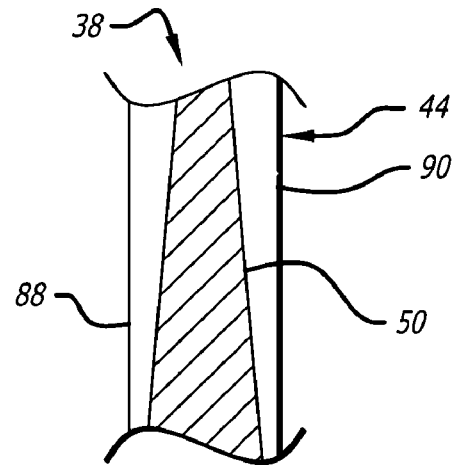

Similarly, with reference now to FIG. 23, there is shown another embodiment of a flexible wall segment 50 having a lower proximal portion 106 and a distal upper portion 108 having tapered inner and outer surfaces so that the flexible wall segment becomes thinner toward the distal end 38 and terminates generally centered between the outside and inside edges 90 and 88 respectively. The distal taper of the present flexible wall segment allows for easier compression of the distal end of the male body portion 36 toward the contracted configuration. Moreover, the substantially symmetrical cross-section of the flexible wall segment will help ensure uniform compression and prevent unwanted buckling of the wall.

Figure 24:
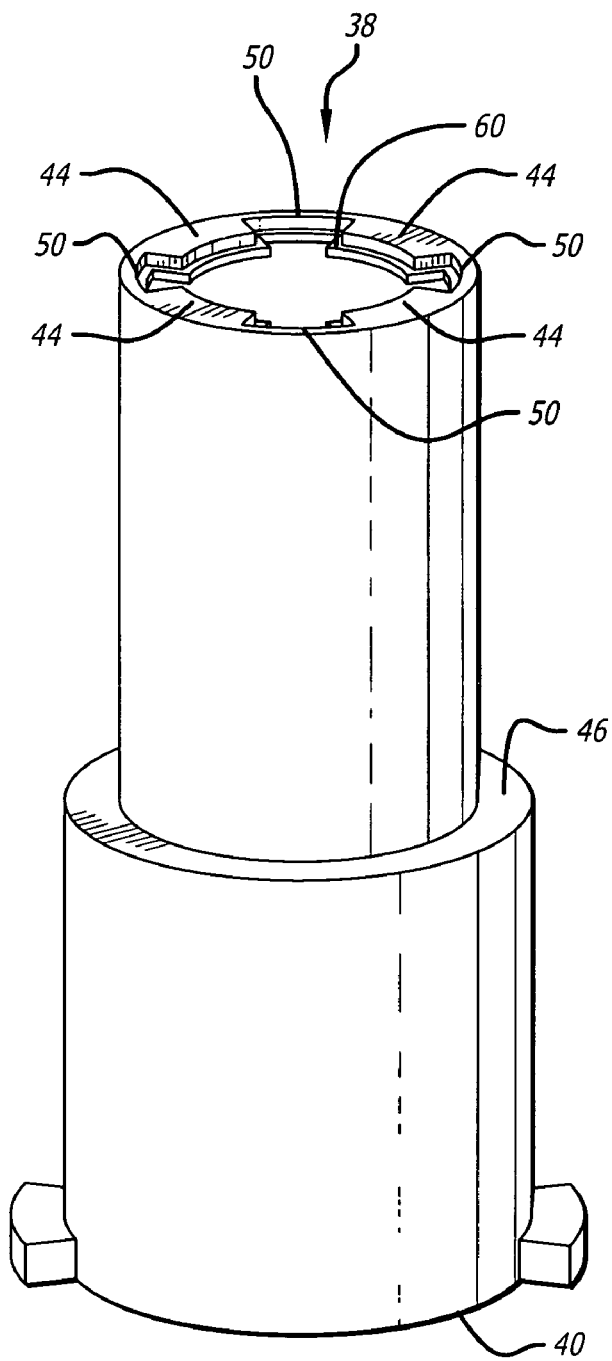
FIG. 24 is a perspective view of an alternate embodiment of an elongated male body having alternate wall segments of reduced thickness to enhance flexibility and permit collapsing the distal end when engaged with a female connector device.
Figure 25:
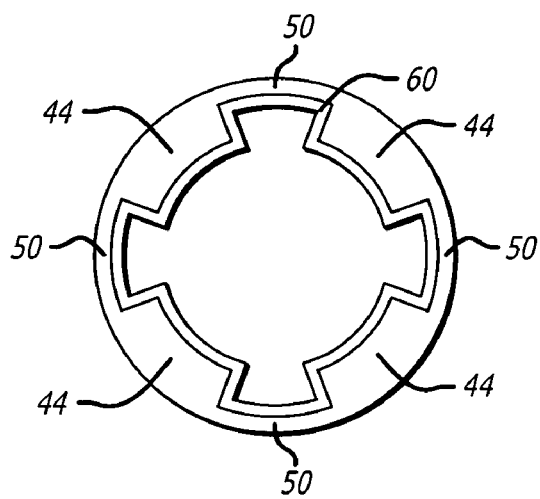
FIG. 25 is an end-on view of the configuration of the wall of the male body portion of FIG. 24 with the closure cap removed so that the alternating segments of more rigid wall segments with more flexible wall segments can be seen.

Although shown and described above as having slots with different material forming the flexible wall segments in those slots, other arrangements are possible. Referring now to FIG. 24, there is shown another embodiment of the elongated male body portion 36 that has reduced thickness sections 50 interspaced with rigid wall segments 44 comprising the same material but thicker. The reduced thickness sections and thicker sections terminate at the base 46 as in other embodiments. In one embodiment, all walls, both rigid and flexible, are of substantially uniform cross-sectional thickness at the base. This provides structural integrity at the proximal end of the tubular body. The reduced thickness sections 50 formed in the tubular male body provide increased radial flexibility at its distal end 38. By forming the reduced thickness sections within the wall of the male body portion as one continuous tubular structure, the desired radial compressibility is achieved so as to allow rim elements 48 at the distal end to flex radially inwardly upon insertion into a female connector. The outside surface of the male body portion 36 has a continuous surface that helps provide surface-to-surface engagement with the inside surface of the female connector, thereby forming a tight seal during connection. A distal-end view is shown in FIG. 25.

In yet another embodiment that is not shown, the elongated male body portion 36 is formed with a tubular wall 44 that is substantially uniform in diameter and wall thickness along its entire length. The body is made of a compressible, resilient material such that the continuous distal rim 48 may be oversized as compared to the inner diameter of the female connector and be compressed radially inwardly toward the contracted configuration when inserted in the female connector. Such a material, as for example, medical grade thermoplastic rubber, is substantially resilient so as to return to its expanded configuration upon removal from the female connector, but also conforms to the inside surface of the female connector when inserted therein so as to maintain a positive seal between the engaged connectors. A mounting ridge would be included at the distal end for receiving the closure cap shown in other figures, except that the closure cap will not have flexible wall segments formed as part of it.

In yet another embodiment, the elongated male body portion of the male connector device is formed with spaced-apart undulations to provide a reduced thickness cross-section about the body. The undulations cooperate to form flexible wall segments between the remaining relatively rigid wall segments, thereby allowing for radial compression of the overall tubular body during engagement with a female connector device. The undulations terminate short of the base so that the base provides structural integrity and biasing of the reduced in thickness male body portion.

Figure 26:
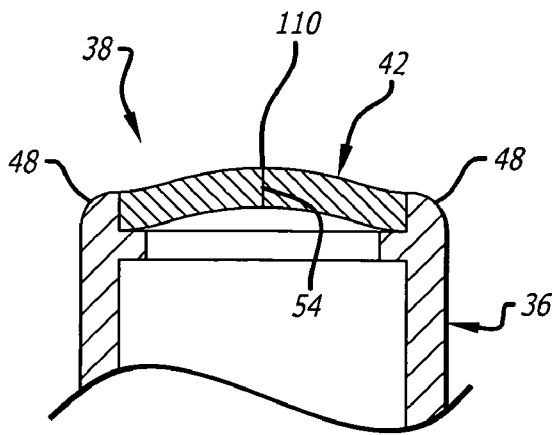
FIG. 26 presents a side, cross-sectional view of the distal end of the male connector device showing a closure cap biased axially outward at its center in its natural configuration.

Referring now to FIG. 26, there is shown a cross-sectional view of the male body portion 36 in its natural, at-rest, expanded configuration. As can be seen, the center 110 of the closure cap 42 is configured to have a slightly axially outward bias or bow. In this way, when the male connector device 30 is inserted into a female connector device and the relatively rigid wall segments 44 are flexed radially inwardly compressing the closure cap to open the slit, it will be appreciated that the axially outward pre-bias of the closure cap causes the cap to further flex or bow axially outwardly into a convex configuration, as shown in FIG. 11.

Figure 27:
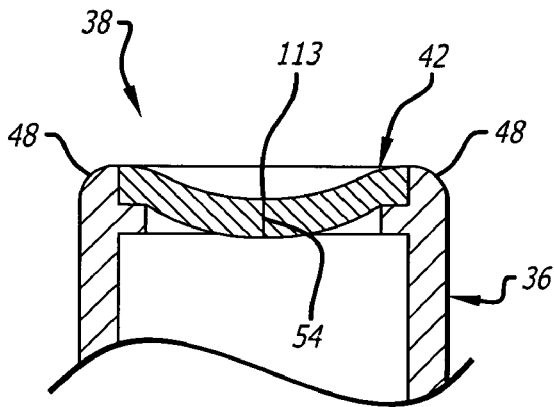
FIG. 27 presents a side, cross-sectional view of the distal end of the male connector device showing a closure cap biased axially inward at its center in its natural configuration.

Referring now to FIG. 27, there is shown an elongated male body portion 36 having an alternative embodiment closure cap 42 sealingly installed thereon. The closure cap is again formed as being generally annular so as to be flush along the ridge 60 of the distal end 38 and has a single slit aperture 54 oriented to be generally parallel to the flexible wall segments 50. However, the closure cap 42 is formed having a slightly axially inward bias or bow at its center 112. As such, when the male connector device 30 is inserted into a female connector device and radially inward compression forces are exerted against the relatively rigid wall segments 44 in the vicinity of the rim elements 48, the axially inward pre-bias of the closure cap causes the cap 42a to further bow axially inwardly into a concave configuration, as shown in FIG. 12.

Figure 28:
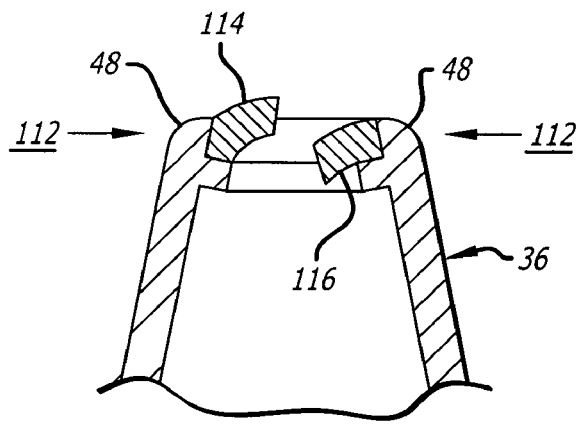
FIG. 28 presents a side, cross-sectional view of the distal end of the male connector device of FIG. 2 in the contracted configuration showing the slit of the closure cap that was biased axially inward on one side and axially outward on the other side open for fluid flow.

Referring now to FIG. 28, an alternative embodiment of the closure cap 42 is shown. In this embodiment, the closure cap is generally planar when the male body portion 36 is in its natural, at-rest, expanded configuration, as shown in FIG. 2. Again, the resealable aperture or slit 54 is formed in the cap so as to be generally parallel to the flexible wall segments 50 and to the direction of the radial compression forces indicated by the directional arrows 112 in FIG. 28. The cap is formed such that one side 114 is biased to flex axially outwardly upon compression, and the opposite side 116 of the cap is biased to flex axially inwardly upon compression. In this way when the male body portion 36 is radially compressed, side 102 of the closure cap 42 is flexed or bowed axially outwardly and opposite side 104 is flexed axially inwardly. The slit 54 is thus opened and a flow path is created between the male and female connectors.

Figure 29:
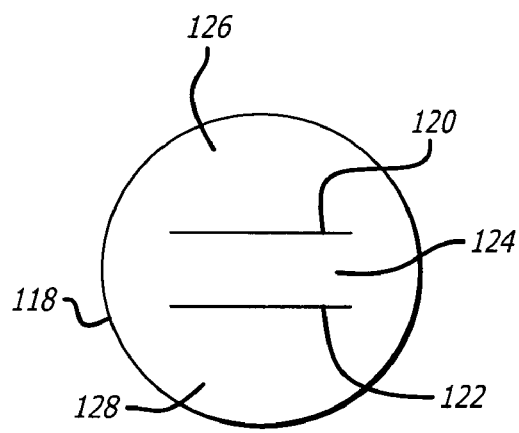
FIG. 29 is an end-on view of a closure cap having two parallel and offset slits for fluid flow when opened.
Figure 30:
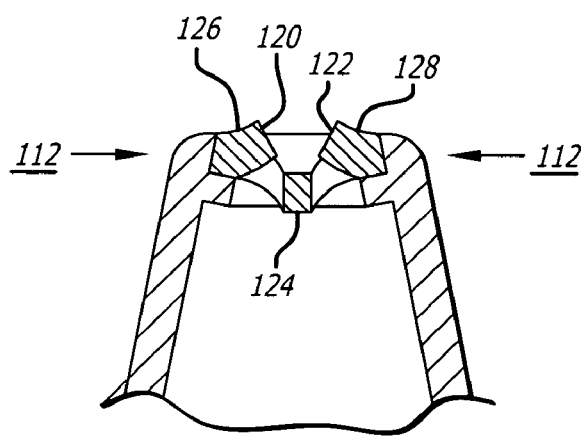
FIG. 30 presents a side, cross-sectional view of the distal end of the male connector device of FIG. 2 having the closure cap of FIG. 29 in the contracted configuration showing the membrane material outside of the slits that were biased axially outward open and the central membrane between the slits that was biased axially inward also open for fluid flow.

Turning now to FIG. 29, there is shown another alternative embodiment closure cap 118 installed on an elongated body 36 of the male connector device 30. The alternative closure cap is formed having two parallel, spaced-apart slits 120 and 122 again generally oriented to be parallel to the flexible wall segments 50. By having two offset slits, the alternative closure cap is essentially divided into two opposite sides with a central membrane 124 portion between the two sides. As seen in FIG. 29, the alternative closure cap is configured so as to be generally planar in its natural configuration. Then, as shown in FIG. 30, when the distal end of the male body portion is radially compressed in the direction of arrows 112, the central portion 124 of the alternative closure cap 118 will flex axially inwardly while the opposite sides 126 and 128 will flex axially outwardly to open the two slits 120 and 122 and create two flow paths therethrough. In one embodiment, the thickness of the closure cap may be increased in the area of the central membrane portion 124 to further facilitate its flexing inwardly with respect to the opposite adjacent sides.

Figure 30A:
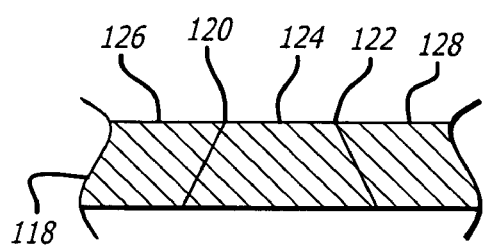
FIG. 30a presents a cross section view of an embodiment of the angled slits that may be used in FIG. 30. Due to the angle of the slits, resistance against internal pressure possibly causing the slits to open and permit undesired fluid flow is prevented.

FIG. 30a provides one embodiment where the slits 120 and 122 are formed at an angle so as to resist internal pressure from possibly causing undesired fluid flow through the slits. If internal pressure builds up against the center section 124, movement of the center section to open will be resisted by the two outer sections 126 and 128 since each outer section has material overlapping the outer portion of the middle section due to the angled slits.

Figures 31, 32:
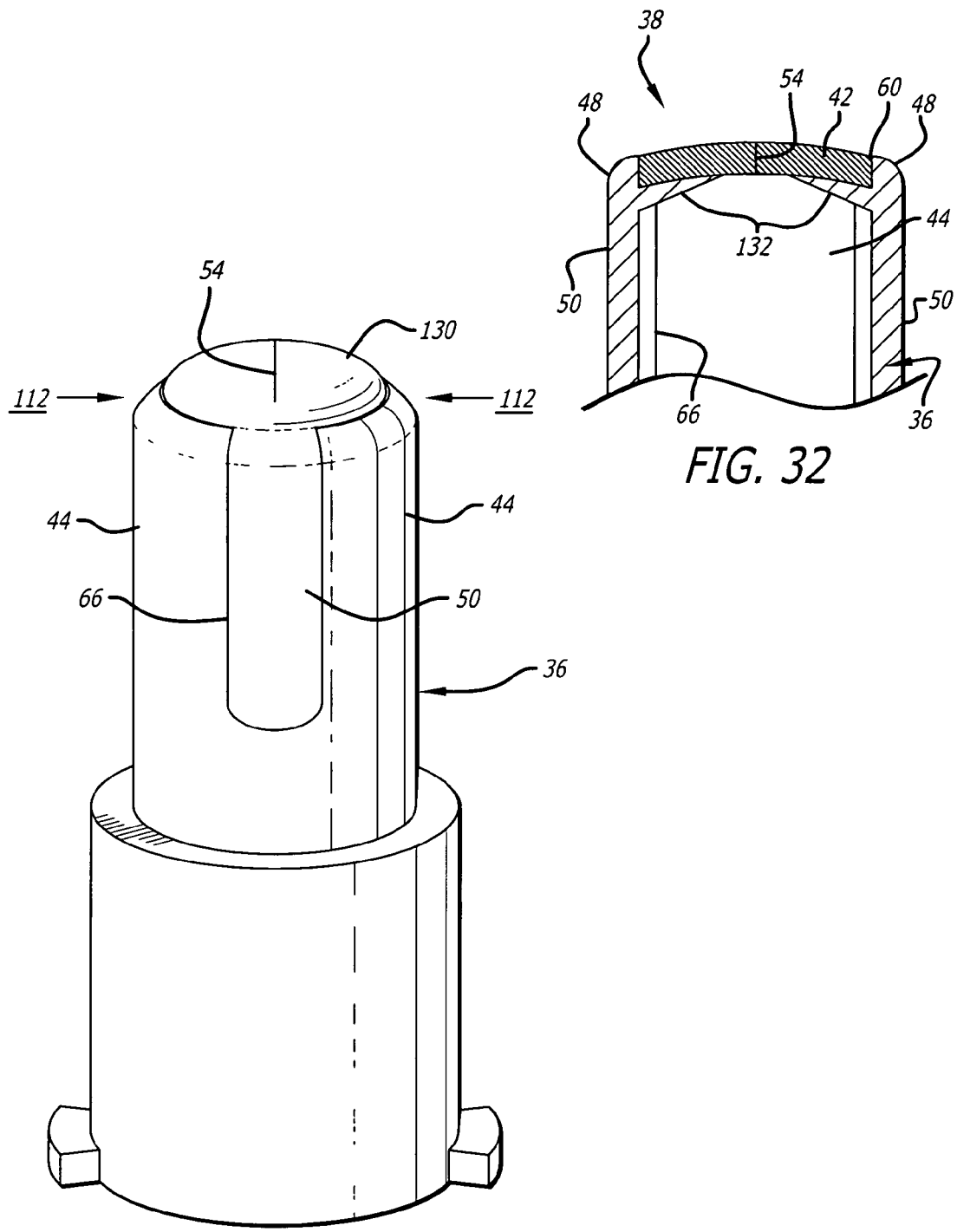
FIG. 31 shows the male connector device of FIG. 2 with the slit in the closure cap rotated by ninety degrees to be parallel with relatively rigid wall segments.
FIG. 32 is an enlarged cross-sectional view of the distal end of the elongated male body showing a closure cap that is slightly bulged axially outward at its center with fillets between the flexible wall segments and the closure cap.

In an alternative embodiment as shown in FIG. 31, the closure cap 42 has a single slit 54 however when the cap is mounted to the male body 36, the slit is oriented so that the ends of the slit are adjacent the flexible wall segments 50 and the slit is therefore generally perpendicular to the flexible wall segments 50. The slit will also then be generally perpendicular to the direction of the radial compression forces, as indicated by arrows 112, exerted on the relatively rigid wall segments 44 when the male connector device 30 is inserted within a female connector device. Further, as shown in FIG. 31, the center 130 of the closure cap is configured to have a slightly axially outward bias or bow so that when the male body portion and the closure cap are radially compressed, the axially outward pre-bias of the closure cap causes the cap to further flex or bow axially outwardly into a convex configuration opening the slit. Though the compression is perpendicular to the axis of the slit, as shown by the arrows 112, the reduction in the annular perimeter of the body and of the closure cap as it is compressed results in the opening of the slit.

Although not shown, in another alternative embodiment, the closure cap 42 having a slit aperture 54 can be mounted such that the ends of the slit are located adjacent flexible wall segments 50 and will therefore be oriented generally perpendicular to the force on the rigid wall segments 44, as shown in FIG. 31. However in this embodiment, the center of the closure cap is configured with a slightly axially inward bias or bow (similar to that shown in FIG. 27) so that when the male body portion 36 and the cap are radially compressed, the axially inward pre-bias causes the cap to further flex or bow axially inwardly into the concave configuration shown in FIG. 12. The reduction in the annular perimeter of the body and the closure cap, as it is compressed, causes the inward displacement of the cap's center to open the slit.

Turning now to FIG. 32, the distal end 38 of the male connector device is shown in cross section so that the mounting of the closure cap 42 to the rim elements 48 can be more clearly seen. In this embodiment, the closure cap has a slightly axially outward pre-biased flex but is mounted within the mounting ridge 60. The flexible wall segments 50 are positioned radially outwardly within each notch 66 and are configured at their distal ends with radially inwardly projecting fillets 132 adjoining the closure cap. Because the fillets interconnect the flexible wall segments and the closure cap, they provide added pressure to direct the closure cap axially outwardly as the flexible wall segments shift radially inwardly during engagement with a female connector device. The fillets therefore cooperate with the flexible wall segments to flex the closure cap toward its convex, dome-shaped configuration to thereby open the slit as shown in FIG. 11.

As the male connector device 30 is withdrawn from the female connector device, the reverse action takes place between the flexible wall segments 50, the fillets 132, and the closure cap 42. That is, as the radial compression forces are removed from the male body 36, the relatively rigid wall segments 44, flexible wall segments 50, and base 46 cooperate to flex the body back to its natural, expanded configuration. The flexible wall segments flex generally radially outwardly and return to their natural configuration. In so doing, the interconnecting fillet 132 serves to help direct the closure cap 42 back to its at-rest configuration shown in FIG. 32. Moreover, it will be appreciated that the radially-outward movement of the flexible wall segments during the return of the body to its natural, at-rest, expanded configuration also increases the volume within the male connector device, thereby creating a small partial vacuum. This partial vacuum creates a draw-back effect that can draw residual fluid on or about the resealable aperture 54 into the male connector as it reseals so as to further keep the fluid in a controlled manner and prevent exposure of the fluid to both care givers and patients.

Similarly to the configuration shown in FIG. 32, the closure cap 42 can be biased axially inward and have fillets between the flexible wall segments and the closure cap. When biased inward, such as is shown in FIG. 27, the distal end 38 of the male connector device 30 will take on the configuration shown in FIG. 12 when contracted due to engagement with a female connector device. The fillet interconnecting the distal ends of the respective flexible wall segments with the closure cap then serves to pull the closure cap inwardly to open the slit. Similarly, when the male connector device 30 is disconnected from the female connector and the radial compression forces are removed from the male body portion 36 so that it can return to its natural, at-rest, expanded configuration, the radially-outward movement of the flexible wall segments will also shift the fillets radially outwardly to cooperate in flexing the closure cap outwardly toward its natural, at-rest configuration to reseal the aperture 54.

Figure 33:
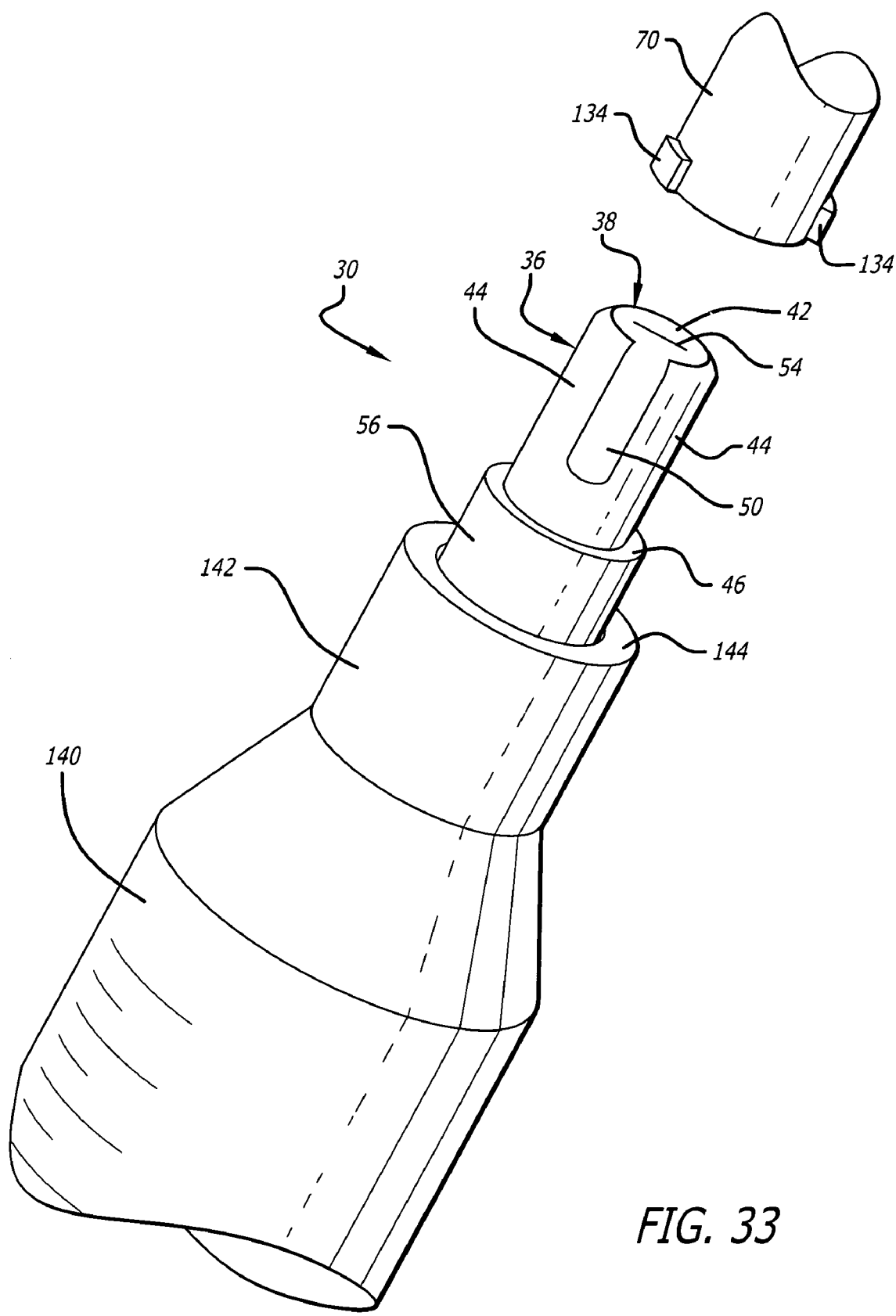
FIG. 33 shows an application of the male connector device in accordance with the invention with a syringe and showing the male body aligned with a female connector device for engagement.

Turning now to FIG. 33, there is shown a partial perspective view of and embodiment of the male connector device 30 in accordance with the present invention connected to a medical syringe 140. The distal end 142 of the syringe is formed with a male Luer connector (not shown) configured to sealingly engage the female Luer connector 52 formed at the proximal end of the male connector device, and may be additionally configured with a collar 144 concentrically about the male Luer connector of the syringe and having internal threads (not shown) configured to threadably engage external thread portions (not shown) formed on the proximal base of the male connector device's female connector. Once the male connector device is connected to the syringe, the self-sealing closure cap 42 prevents the escape of any fluid from the syringe while the connector device is disconnected and in its natural, at-rest, expanded configuration as shown.

With continued reference to FIG. 33, there is shown adjacent the male connector device 30 a female connector 70 of a patient's IV line in position for connection, as when a fluid in the syringe is to be administered to the patient or a fluid from the patient is to be withdrawn into the syringe. The female connector device includes external thread elements 134 Thus, as explained with respect to FIGS. 7 through 9, when the oversized male body portion 36 is inserted within the female connector, the relatively rigid wall segments 44 are flexed radially inwardly, as allowed by the flexible wall segments 50, to compress the closure cap 42 and open the slit 54, thereby creating a flow passage completely through the male connector device 30 and with the female connector 70. Then, after the desired fluids have been infused or aspirated, the male connector device is simply disconnected from the female connector, allowing the male body portion to return to its expanded configuration and closing the slit to reseal the male connector device and prevent the escape of fluid from the syringe. Thus, the male connector device in accordance with the present invention provides controlled dispensing from and withdrawal into a syringe or other such medical device or dispenser without the use of a sharpened needle. Further, it will be appreciated that the male connector device is easy to wipe and keep sanitary, as all engagement surfaces are exposed and easily accessible upon disconnection of the device from the female connector.

Figure 34:
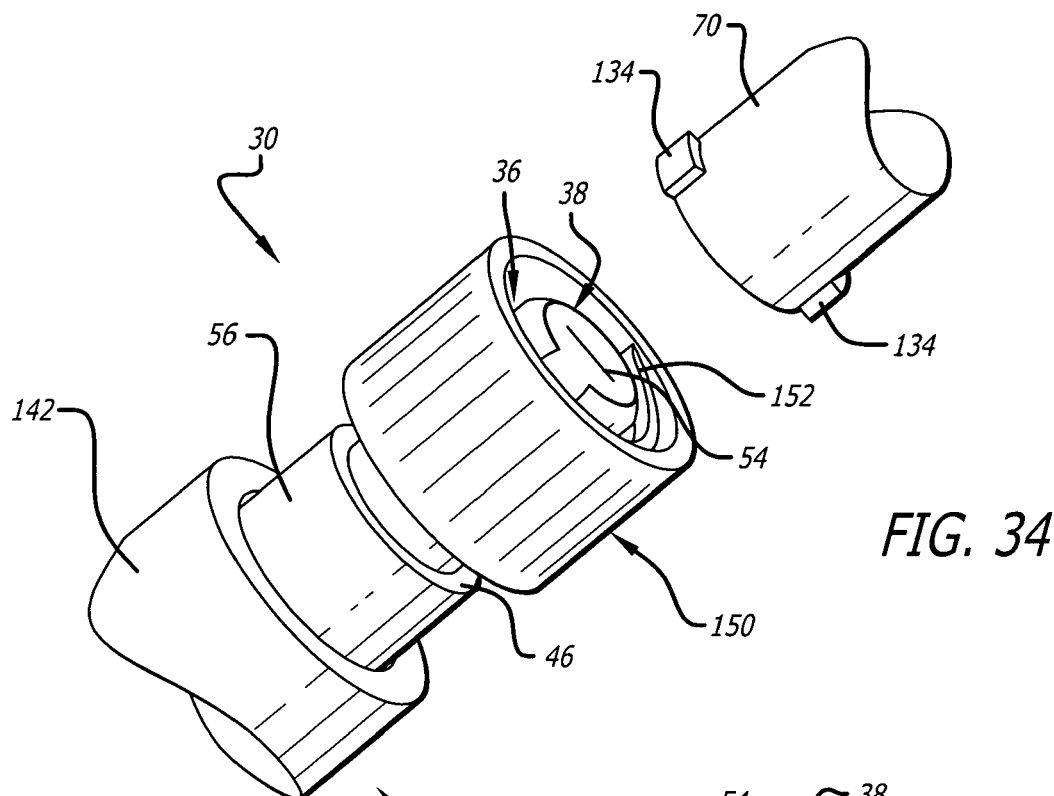
FIG. 34 is a male connector device similar to FIG. 33 with a threaded collar surrounding the male body portion for more secure engagement with a female connector.

FIG. 34 shows the same male connector device 30 as in FIG. 33 except with the addition of a threaded collar 150 surrounding the male body 36 and having internal threads 152. The collar's threads are used for engaging the external thread segments 134 of the female connector 70 to firmly secure the male connector and female connector devices together.

Figure 35:
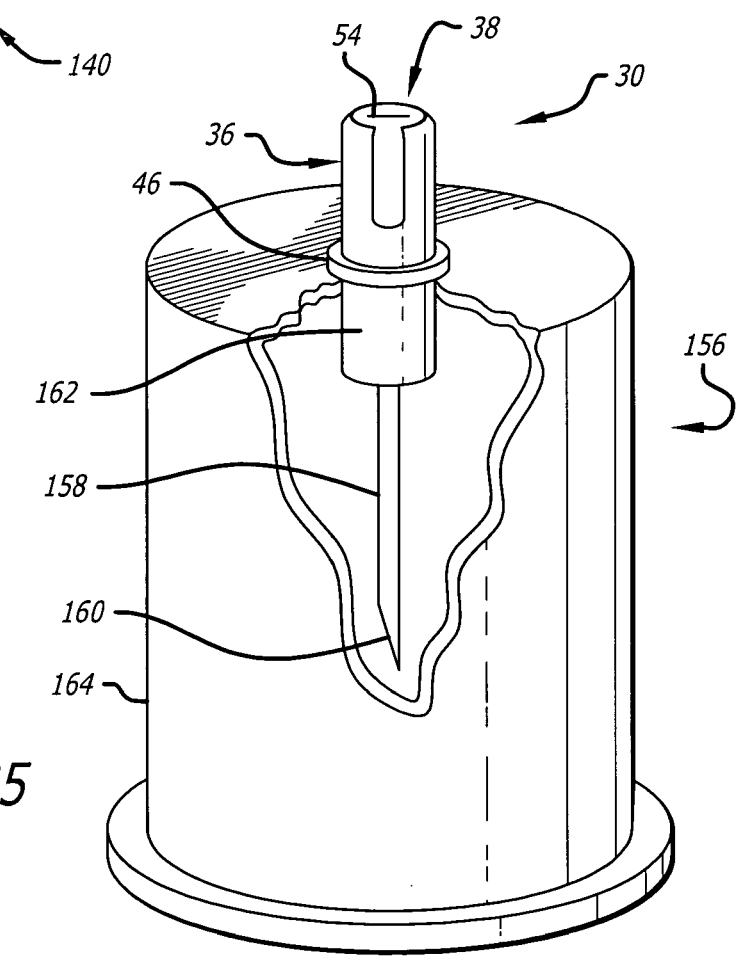
FIG. 35 shows an application of the male connector device in accordance with the invention with a blood collection device having a shield and sharpened cannula within the shield for use of blood collection tubes.

FIG. 35 shows yet another alternative embodiment in which the male connector device 30 has a blood collection device 156 mounted opposite the base 46 from the male body portion 36, rather than a conventional female Luer connector.

The blood collection device, which is known and used in the art, comprises a cannula 158 having a sharpened tip 160 and is securely embedded in the cannula mount 162. A shield 164 is mounted about the needle to protect clinicians and patients from accidental needle sticks and to support a blood collection tube in some cases. The male body portion 36 of the connector device 30 may be connected to a female connector device of a patient's IV line, as discussed above, to open the slit 54 in the closure cap and create a flow path between the patient's IV line and the blood collection 158. Once the requisite amount of blood has been extracted, the tube is removed form the blood collection device 156 and the male body portion 36 may be disconnected from the female connector device. Upon disconnection from the female connector, the male body portion expands to its natural, at-rest configuration causing the slit 54 to reseal and trap all blood and any other fluids within the male connector device for safe disposal. Thus, in this embodiment of the present invention, the self-sealing, needle-free oversized male connector serves to safely and easily connect to and disconnect from a female Luer connector of a patient's IV line for the effective and controlled administration and/or withdrawal of fluids.

Although the present invention has been described in terms of certain preferred embodiments, other embodiments may also exist that are within the scope of the invention. Accordingly, the scope of the invention is intended to be defined only by reference to the appended claims. While the variations of the flexible wall segments, closure cap, and resealable apertures have been described and shown, it is to be understood that these variations are merely exemplary of the present invention and are not meant to be limiting on the scope of the invention.

What is claimed is:

1. A self-sealing male connector device for connection with a female connector device, the female connector device having an inner engagement surface that is smaller in diameter than the male connector device, the self-sealing male connector device comprising:
    a male body having a first end, the first end having a first diameter when in its natural disconnected configuration and a second diameter smaller than the first diameter when the first end is connected with the smaller-diameter inner engagement surface of the female connector device and is thereby forced to a contracted configuration; and
    a closure cap disposed at the first end of the male body that closes the male body against fluid flow, the closure cap having a diameter and being mounted to the male body so that the closure cap diameter varies with diameter variations of the first end of the male body, the closure cap having an aperture formed such that the aperture is closed when the male body is disconnected from the female connector device and is in its natural disconnected configuration and the aperture is open to permit fluid flow through the closure cap when the diameter of the closure cap is caused to contract as the male body is moved to its contracted configuration due to connection with the smaller-diameter female connector device;
    wherein the male body comprises a tubular wall extending to the first end of the male body, the tubular wall being formed of a first segment and a second segment with the second segment being more flexible than the first segment.

2. The self-sealing male connector device of claim 1 wherein the male body further comprises a second end and a fluid passageway providing fluid communication between the first end and the second end.

3. The self sealing male connector device of claim 1 wherein the second segment has a wall thickness that is thinner than a wall thickness of the first segment thereby making the second segment more flexible than the first segment.

4. The self sealing male connector device of claim 1 wherein the second segment is formed of a resilient material constituting a web.

5. The self sealing male connector device of claim 4 wherein the closure cap and web are formed as one piece.

6. The self sealing male connector device of claim 1 wherein the male body comprises a tubular wall extending to the first end of the male body, the tubular wall including at least two spaced-apart relatively rigid wall segments that project axially and form at least a portion of a rim at the first end.

7. The self sealing male connector device of claim 6 wherein the tubular wall includes flexible wall segments connecting the rigid wall segments together, the flexible wall segments facilitating the male body moving to the contracted configuration.

8. The self sealing male connector device of claim 1 wherein the closure cap is mounted to the first end so that as the diameter of the closure cap contracts as the diameter of the first end contracts, a center section of the closure cap containing the aperture is displaced in a longitudinal axial direction thereby causing the aperture to open to permit fluid flow through the closure cap.

9. The self sealing male connector device of claim 1 wherein the aperture comprises a slit.

10. The self sealing male connector device of claim 1 wherein the male body comprises a tubular wall extending to the first end of the male body, the tubular wall including a lengthwise notch extending axially from the first end whereby the notch facilitates the male body moving to the contracted configuration.

11. The self sealing male connector device of claim 10 wherein two lengthwise notches are formed in the tubular wall substantially opposite one another extending axially from the first end and are configured to be substantially symmetrical about a central longitudinal axis of the male body.

12. The self sealing male connector device of claim 1 wherein the male body further comprises a second end that is connected to a syringe.

13. The self-sealing male connector device of claim 1 wherein the male body further comprises a second end that is configured as a blood collection device.

14. The self sealing male connector device of claim 1 wherein:
    the male body comprises a tubular wall extending to the first end of the male body with an outer edge of the tubular wall at the first end including a rim that defines an opening;
    the rim has a rounded outer edge whereby connection of the first end with the female connector device is facilitated;
    the rim flexes between a natural open configuration and the contracted configuration; and
    the rim is in the contracted configuration when the male body is inserted into the female connector.

15. A self sealing male connector device for connection with a female connector device, the female connector device having an inner engagement surface that is smaller in diameter than the male connector device, the self sealing male connector device comprising:
    a male body having a first end, the first end having a first diameter when in its natural disconnected configuration and a second diameter smaller than the first diameter when the first end is connected with the smaller-diameter inner engagement surface of the female connector device and is thereby forced to a contracted configuration, the male body comprising a tubular wall extending to the first end of the male body, the tubular wall comprising two lengthwise notches are formed in the tubular wall substantially opposite one another extending axially from the first end and are configured to be substantially symmetrical about a central longitudinal axis of the male body with a web formed within the notches, wherein the tubular wall forms first wall segments between the notches and the web forms second wall segments in the notches with the second wall segments being more flexible than the first wall segments, the flexible wall segments facilitating the male body moving to the contracted configuration, and wherein, an outer edge of the tubular wall at the first end includes a rim that defines an opening with the rim having a rounded outer edge whereby connection of the first end with the female connector device is facilitated; and a closure cap disposed at the first end of the male body that closes the opening of the male body against fluid flow, the closure cap having a diameter and being mounted to the male body so that the closure cap diameter varies with diameter variations of the first end of the male body, the closure cap having an aperture formed such that the aperture is closed when the male body is disconnected from the female connector device and is in its natural disconnected configuration and the aperture is open to permit fluid flow through the closure cap when the diameter of the closure cap is caused to contract as the male body is moved to its contracted configuration due to connection with the smaller-diameter female connector device;

wherein the closure cap and the web are formed as one piece.

16. The self sealing male connector device of claim 15 wherein the aperture comprises a slit.

17. The self sealing male connector device of claim 15 wherein the male body further comprises a second end that is connected to a syringe.

18. A method of connecting a self sealing male connector device to a female connector device, the female connector device having an inner engagement surface that is smaller in diameter than the male connector device, the method comprising:

inserting the male connector device into the female connector far enough so as to engage a first end of the self sealing male connector device with the smaller diameter female engagement surface and thereby contract the diameter of the first end of the male connector device; and opening an aperture in the first end of the self sealing male connector device as a result of the diameter of the first end being contracted to allow fluid flow therethrough;

wherein the male connector device comprises a tubular wall extending to the first end of the male connector device, the tubular wall being formed of a first wall segment and a second wall segment with the second wall segment being more flexible than the first segment.

19. The method of claim 18 wherein the step of inserting further comprises contracting the first and second wall segments toward each other and flexing third and fourth wall segments located between the first and second wall segments to allow for contraction of the first and second wall segments.

20. The method of claim 19 further comprising the step of forming a closure cap located at the first end and the third and fourth wall segments as one piece.

* * * * *